US011883058B2

(12) United States Patent
Netzel et al.

(10) Patent No.: US 11,883,058 B2
(45) Date of Patent: Jan. 30, 2024

(54) JAW MEMBERS, END EFFECTOR ASSEMBLIES, AND ULTRASONIC SURGICAL INSTRUMENTS INCLUDING THE SAME

(71) Applicant: Covidien LP, Mansfield, MA (US)

(72) Inventors: Kenneth E. Netzel, Loveland, CO (US); David J. Van Tol, Boulder, CO (US)

(73) Assignee: Covidien LP, Mansfield, MA (US)

( * ) Notice: Subject to any disclaimer, the term of this patent is extended or adjusted under 35 U.S.C. 154(b) by 157 days.

(21) Appl. No.: 16/803,043

(22) Filed: Feb. 27, 2020

(65) Prior Publication Data

US 2020/0305925 A1 Oct. 1, 2020

Related U.S. Application Data

(60) Provisional application No. 62/823,762, filed on Mar. 26, 2019.

(51) Int. Cl.
*A61B 17/295* (2006.01)
*A61B 17/32* (2006.01)
(Continued)

(52) U.S. Cl.
CPC .... *A61B 17/320092* (2013.01); *A61B 17/282* (2013.01); *A61B 17/295* (2013.01);
(Continued)

(58) Field of Classification Search
CPC .......... A61B 17/320092; A61B 17/295; A61B 2017/00473; A61B 2017/2825;
(Continued)

(56) References Cited

U.S. PATENT DOCUMENTS 1,585,934 A  5/1926  Muir
1,666,332 A  4/1928  Hirsch
(Continued)

FOREIGN PATENT DOCUMENTS

DE  3339322 A1  5/1984
DE  3206381 C2  7/1986
(Continued)

OTHER PUBLICATIONS

Extended European Search Report issued in corresponding European Application No. 20165018.1 dated Jul. 21, 2020, 6 pages.

*Primary Examiner* — Timothy J Neal
*Assistant Examiner* — Mitchell Brian Hoag
(74) *Attorney, Agent, or Firm* — Carter, DeLuca & Farrell LLP

(57) ABSTRACT

A jaw member, end effector assembly including the jaw member and an ultrasonic blade, and an ultrasonic surgical instrument including the end effector assembly are provided. The jaw member includes a structural body and a jaw liner. The structural body includes a pair of proximal flanges and an elongated distal portion extending distally from the proximal flanges. The elongated distal portion includes spaced-apart side rails defining an elongated opening therebetween and interconnected at distal ends thereof via a distal cap. The jaw liner is engaged within the elongated opening and includes a base and first and second arms extending from the base. Each arm defines an inwardly-angled tissue contacting surface. The jaw liner defines a jaw liner compliance feature extending longitudinally therealong between the inwardly-angled tissue-contacting surfaces of the first and second arms to facilitate outward deflection of the first and second arms relative to one another.

23 Claims, 7 Drawing Sheets

(51) Int. Cl.
*A61B 17/28* (2006.01)
*A61B 17/00* (2006.01)
*A61B 17/29* (2006.01)

(52) U.S. Cl.
CPC .............. *A61B 2017/0023* (2013.01); *A61B 2017/00398* (2013.01); *A61B 2017/00473* (2013.01); *A61B 2017/00734* (2013.01); *A61B 2017/2825* (2013.01); *A61B 2017/2926* (2013.01); *A61B 2017/2932* (2013.01); *A61B 2017/2939* (2013.01); *A61B 2017/320075* (2017.08); *A61B 2017/320094* (2017.08)

(58) Field of Classification Search
CPC ....... A61B 2017/320075; A61B 2017/320094; A61B 2017/2945; A61B 17/282
USPC ......................................................... 606/169
See application file for complete search history.

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,971,034 A | 11/1990 | Doi et al. |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,586,973 A | 12/1996 | Lemaire et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |

(56) References Cited

U.S. PATENT DOCUMENTS

| | | |
|---|---|---|
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,025,656 B2 | 9/2011 | Gruber et al. |
| 8,061,359 B2 | 11/2011 | Emanuel |
| 8,062,214 B2 | 11/2011 | Shener et al. |
| 8,157,826 B2 | 4/2012 | Deng et al. |
| 8,419,626 B2 | 4/2013 | Shener-Irmakoglu et al. |
| 8,444,592 B2 | 5/2013 | Williams et al. |
| 8,465,421 B2 | 6/2013 | Finkman et al. |
| 8,500,769 B2 | 8/2013 | Deng |
| 8,528,563 B2 | 9/2013 | Gruber |
| 8,568,424 B2 | 10/2013 | Shugrue et al. |
| 8,574,253 B2 | 11/2013 | Gruber et al. |
| 8,597,228 B2 | 12/2013 | Pyles et al. |
| 8,647,349 B2 | 2/2014 | Gruber et al. |
| 8,663,264 B2 | 3/2014 | Cesarini et al. |
| 8,678,999 B2 | 3/2014 | Isaacson |
| 8,834,487 B2 | 9/2014 | Gruber et al. |
| 8,840,625 B2 | 9/2014 | Adams et al. |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,760 B2 | 6/2015 | Sullivan et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,095,366 B2 | 8/2015 | Sullivan et al. |
| 9,125,550 B2 | 9/2015 | Shener-Irmakoglu et al. |
| 9,155,454 B2 | 10/2015 | Sahney et al. |
| 9,259,233 B2 | 2/2016 | Gruber et al. |
| 9,474,848 B2 | 10/2016 | Williams et al. |
| 9,554,845 B2 * | 1/2017 | Arts ............... A61B 18/1447 |
| 10,376,278 B2 | 8/2019 | Fojtik et al. |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152647 A1 | 6/2010 | Shener et al. |
| 2011/0034943 A1 | 2/2011 | Churchill et al. |
| 2011/0077674 A1 | 3/2011 | Sullivan et al. |
| 2011/0118544 A1 | 5/2011 | Adams et al. |
| 2011/0166419 A1 | 7/2011 | Reif et al. |
| 2012/0067352 A1 | 3/2012 | Gruber et al. |
| 2012/0078038 A1 | 3/2012 | Sahney et al. |
| 2013/0131452 A1 | 5/2013 | Kuroda et al. |
| 2014/0003183 A1 | 1/2014 | Song |
| 2014/0214025 A1 * | 7/2014 | Worrell ............... A61B 18/1445 606/41 |
| 2015/0088181 A1 * | 3/2015 | Van Tol ......... A61B 17/320068 606/169 |
| 2015/0297255 A1 * | 10/2015 | Fan ............... A61B 18/1445 606/41 |
| 2016/0045213 A1 * | 2/2016 | Bertsch ............. A61B 17/2812 606/207 |

(56) References Cited

U.S. PATENT DOCUMENTS

| | | | |
|---|---|---|---|
| 2016/0143658 A1* | 5/2016 | Stokes | A61B 17/320092 606/169 |
| 2016/0354115 A1* | 12/2016 | Smith | A61B 17/3403 |
| 2017/0119415 A1* | 5/2017 | Brandt | A61B 17/2816 |
| 2017/0189046 A1 | 7/2017 | Fojtik et al. | |
| 2017/0238959 A1* | 8/2017 | Craig | A61B 17/320092 |
| 2018/0140352 A1* | 5/2018 | Netzel | A61B 17/320092 |
| 2019/0167342 A1* | 6/2019 | Hancock | A61B 18/1815 |
| 2019/0223939 A1* | 7/2019 | Netzel | A61B 17/29 |
| 2021/0059712 A1* | 3/2021 | Morisaki | B29C 66/02 |
| 2022/0265307 A1* | 8/2022 | Niiyama | A61B 17/282 |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 19751632 C1 | 9/1999 |
| DE | 10320412 A1 | 11/2004 |
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1681022 A1 | 7/2006 |
| GB | 2093353 A | 9/1982 |
| GB | 2311468 A | 10/1997 |
| JP | 2001075416 A | 3/2001 |
| JP | 2002529185 A | 9/2002 |
| JP | 2002538889 A | 11/2002 |
| JP | 2003245247 A | 9/2003 |
| NL | 1006944 C2 | 3/1999 |
| WO | 8101648 A1 | 6/1981 |
| WO | 9211816 A2 | 7/1992 |
| WO | 9307821 A1 | 4/1993 |
| WO | 9315664 A1 | 8/1993 |
| WO | 9426181 A1 | 11/1994 |
| WO | 9505777 A1 | 3/1995 |
| WO | 9510981 A1 | 4/1995 |
| WO | 9510982 A1 | 4/1995 |
| WO | 9522935 A1 | 8/1995 |
| WO | 9530377 A1 | 11/1995 |
| WO | 9611638 A1 | 4/1996 |
| WO | 9626676 A1 | 9/1996 |
| WO | 9709922 A1 | 3/1997 |
| WO | 9717027 A1 | 5/1997 |
| WO | 9719642 A1 | 6/1997 |
| WO | 9724071 A1 | 7/1997 |
| WO | 9734534 A1 | 9/1997 |
| WO | 9735522 A1 | 10/1997 |
| WO | 9809569 A1 | 3/1998 |
| WO | 9810707 A1 | 3/1998 |
| WO | 9846147 A1 | 10/1998 |
| WO | 9903407 A1 | 1/1999 |
| WO | 9903409 A1 | 1/1999 |
| WO | 9907295 A1 | 2/1999 |
| WO | 9911184 A1 | 3/1999 |
| WO | 9939648 A1 | 8/1999 |
| WO | 9944506 A1 | 9/1999 |
| WO | 9960935 A1 | 12/1999 |
| WO | 9012010 A1 | 3/2000 |
| WO | 0028890 A1 | 5/2000 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 0135831 A1 | 5/2001 |
| WO | 0158368 A1 | 8/2001 |
| WO | 0195810 A2 | 12/2001 |
| WO | 02069808 A2 | 9/2002 |
| WO | 03022164 A1 | 3/2003 |
| WO | 03077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 2007044833 A2 | 4/2007 |
| WO | 2012044705 A1 | 4/2012 |

\* cited by examiner

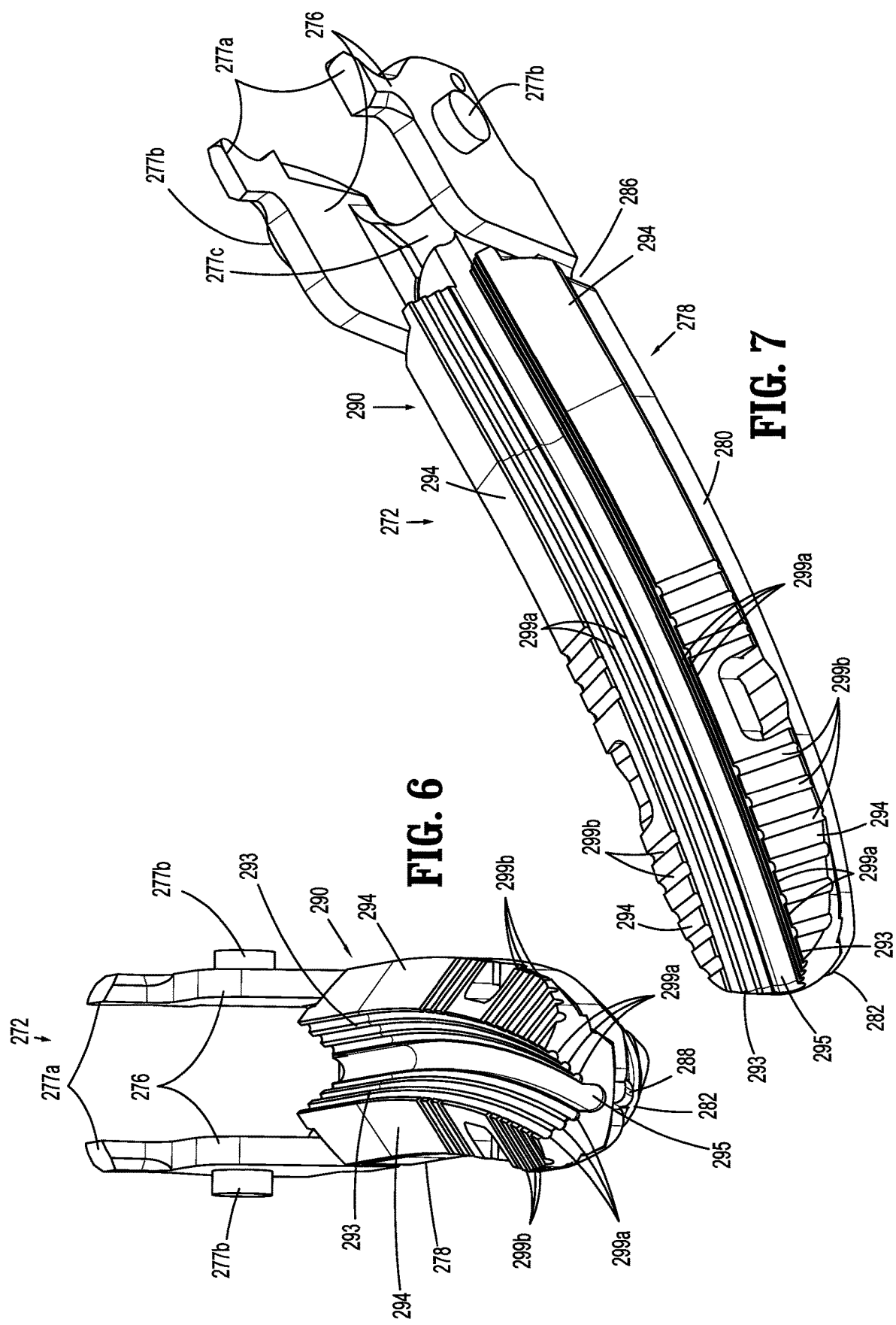

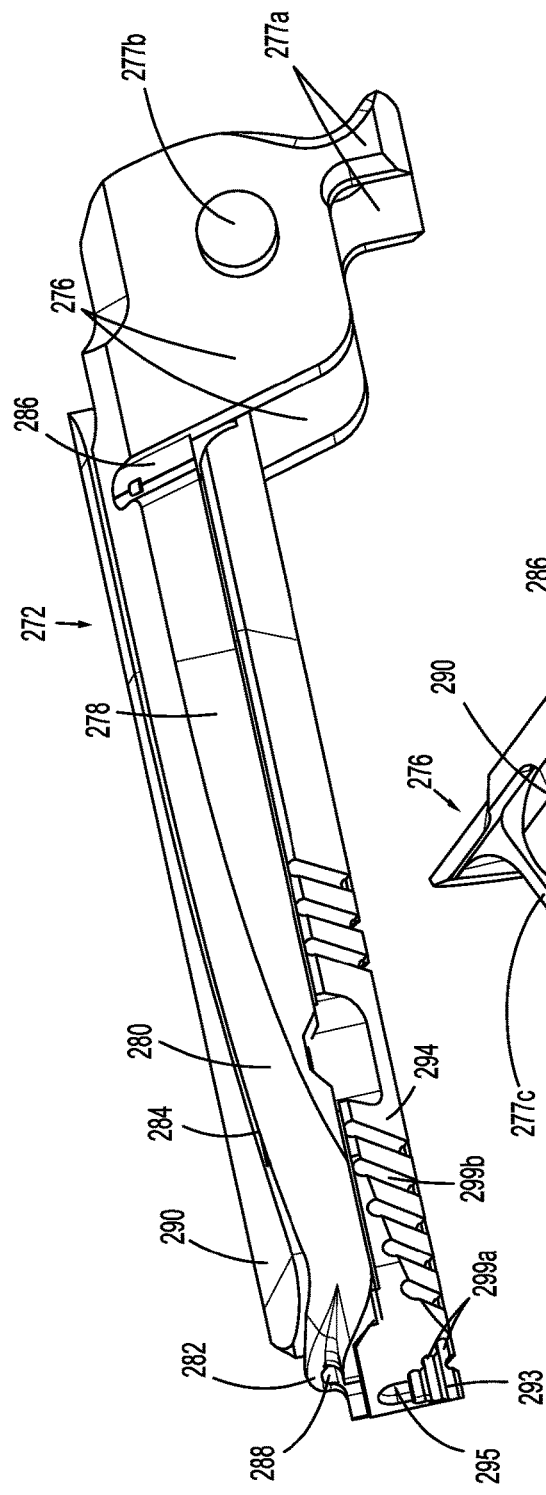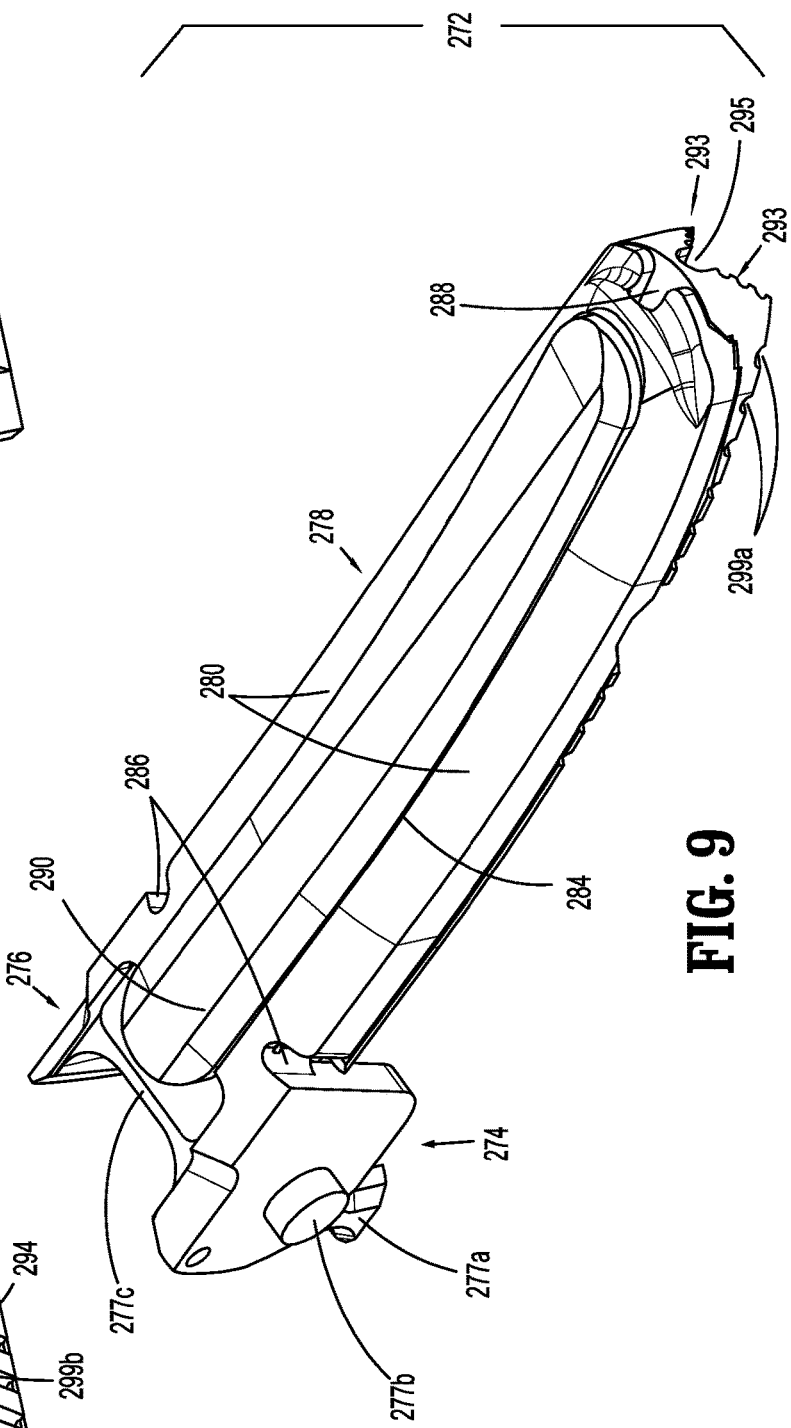

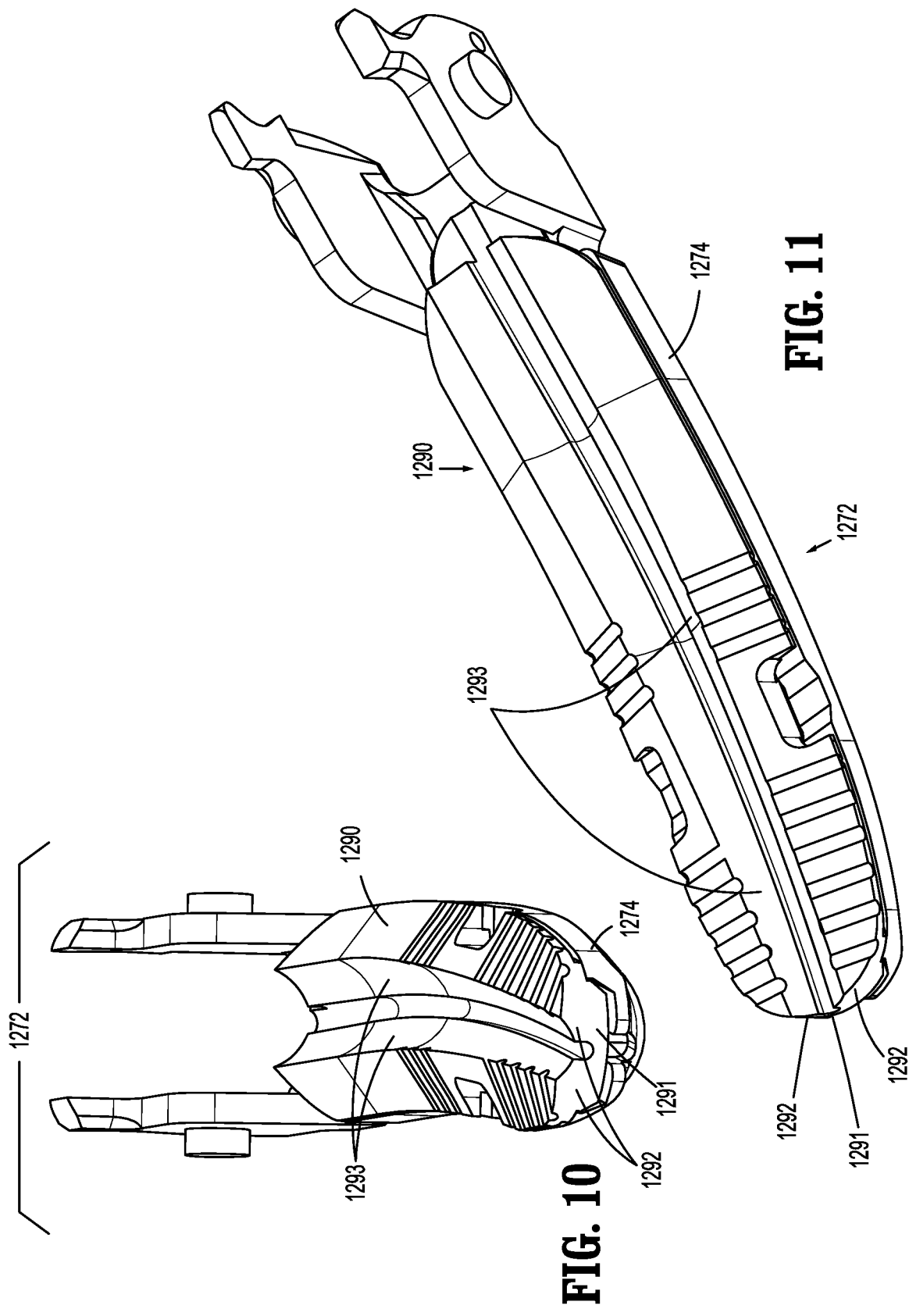

US 11,883,058 B2

JAW MEMBERS, END EFFECTOR ASSEMBLIES, AND ULTRASONIC SURGICAL INSTRUMENTS INCLUDING THE SAME

CROSS-REFERENCE TO RELATED APPLICATIONS

This application claims the benefit of and priority to U.S. Provisional Patent Application Ser. No. 62/823,762 filed Mar. 26, 2019, the entire disclosure of which is incorporated by reference herein.

BACKGROUND

Technical Field

The present disclosure relates to surgical instruments and, more particularly, to jaw members, end effector assemblies, and ultrasonic surgical instruments including the same.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, fulgurate, or otherwise treat tissue.

Typically, an ultrasonic surgical instrument is configured to transmit ultrasonic energy produced by a generator and transducer assembly along a waveguide to an end effector that is spaced-apart from the generator and transducer assembly. With respect to cordless ultrasonic instruments, for example, a portable power source, e.g., a battery, and the generator and transducer assembly are mounted on the handheld instrument itself, while the waveguide interconnects the generator and transducer assembly and the end effector. Wired ultrasonic instruments operate in similar fashion except that, rather than having the generator and power source mounted on the handheld instrument itself, the handheld instrument is configured to connect to a standalone power supply and/or generator via a wired connection.

SUMMARY

As used herein, the term "distal" refers to the portion that is being described which is further from a user, while the term "proximal" refers to the portion that is being described which is closer to a user. Further, to the extent consistent any or all of the aspects detailed herein may be used in conjunction with any or all of the other aspects detailed herein.

In accordance with aspects of the present disclosure, a jaw member configured for use with an ultrasonic surgical instrument is provided including a structural body and a jaw liner. The structural body includes a pair of proximal flanges and an elongated distal portion extending distally from the pair of proximal flanges. The elongated distal portion includes first and second spaced-apart side rails defining an elongated opening therebetween and interconnected at distal ends thereof via a distal cap. The jaw liner is engaged within the elongated opening and includes a base and first and second arms extending from the base. Each arm defines an inwardly-angled tissue contacting surface. The jaw liner defines a jaw liner compliance feature extending longitudinally therealong between the inwardly-angled tissue-contacting surfaces of the first and second arms to facilitate outward deflection of the first and second arms relative to one another.

In an aspect of the present disclosure, the jaw liner compliance feature is an elongated channel.

In another aspect of the present disclosure, the first and second spaced-apart side rails define first and second structural body compliance features configured to facilitate outward deflection of the first and second spaced-apart side rails relative to one another, thus permitting further outward deflection of the first and second arms of the jaw liner relative to one another.

In yet another aspect of the present disclosure, the first and second structural body compliance features are cut-outs defined within the first and second spaced-apart side rails towards proximal ends thereof.

In still another aspect of the present disclosure, the distal cap of the structural body defines a third structural body compliance feature configured to facilitate outward deflection of the first and second spaced-apart side rails relative to one another, thus permitting further outward deflection of the first and second arms of the jaw liner relative to one another.

In still yet another aspect of the present disclosure, each of the inwardly-angled tissue contacting surfaces of the jaw liner includes a plurality of transversely spaced-apart, longitudinally-extending grooves defined therein.

An end effector assembly of an ultrasonic surgical instrument provided in accordance with aspects of the present disclosure includes an ultrasonic blade defining a tissue-contacting surface and a jaw member pivotable relative to the ultrasonic blade between an open position and a clamping position. The jaw member includes a structural body including a pair of proximal flanges and an elongated distal portion extending distally from the pair of proximal flanges. The elongated distal portion includes first and second spaced-apart side rails defining an elongated opening therebetween and interconnected at distal ends thereof via a distal cap. The jaw member further includes a jaw liner engaged within the elongated opening. The jaw liner defines first and second inwardly-angled tissue contacting surfaces configured to oppose the tissue-contacting surface of the ultrasonic blade in the clamping position of the jaw member. The jaw liner defines a jaw liner compliance feature extending longitudinally therealong between the inwardly-angled tissue-contacting surfaces to facilitate outward deflection of the inwardly-angled tissue-contacting surfaces relative to one another to thereby tension tissue clamped between the jaw member and the ultrasonic blade.

In an aspect of the present disclosure, the tissue-contacting surface of the ultrasonic blade includes first and second tissue-contacting surface portions having an apex disposed therebetween. In such aspects, the first and second inwardly-angled tissue contacting surfaces of the jaw liner may be configured to oppose the first and second tissue-contacting surface portions of the ultrasonic blade and the apex of the ultrasonic blade is configured to oppose the jaw liner compliance feature of the jaw liner in the clamping position of the jaw member. The jaw liner compliance feature may be an elongated channel.

In another aspect of the present disclosure, the first and second spaced-apart side rails define first and second structural body compliance features configured to facilitate outward deflection of the first and second spaced-apart side rails relative to one another, thus permitting further outward deflection of the first and second inwardly-angled tissue contacting surfaces of the jaw liner relative to one another.

In still another aspect of the present disclosure, the first and second structural body compliance features are cut-outs defined within the first and second spaced-apart side rails towards proximal ends thereof.

In yet another aspect of the present disclosure, the distal cap of the structural body defines a third structural body compliance feature configured to facilitate outward deflection of the first and second spaced-apart side rails relative to one another, thus permitting further outward deflection of the first and second inwardly-angled tissue contacting surfaces of the jaw liner relative to one another.

In still yet another aspect of the present disclosure, each of the inwardly-angled tissue contacting surfaces of the jaw liner includes a plurality of transversely spaced-apart, longitudinally-extending grooves defined therein.

An ultrasonic surgical instrument provided in accordance with aspects of the present disclosure includes a housing, an ultrasonic transducer supported by the housing, a movable handle pivotably coupled to the housing, and an elongated assembly extending distally from the housing. The elongated assembly includes a support sleeve extending distally from the housing, a drive sleeve operably coupled to the movable handle within the housing and extending distally from the housing and slidable relative to the support sleeve, an ultrasonic waveguide operably coupled to the ultrasonic transducer within the housing and extending distally from the housing through the support and drive sleeves, and an end effector assembly disposed at a distal end of the support sleeve. The end effector assembly includes an ultrasonic blade extending distally from the ultrasonic waveguide and a jaw member pivotable relative to the ultrasonic blade between an open position and a clamping position. The jaw member includes structural body including a pair of proximal flanges pivotably coupling the structural body to the support sleeve and operably coupling the structural body to the drive sleeve. The structural body further includes an elongated distal portion extending distally from the pair of proximal flanges. The jaw member further includes a jaw liner engaged with the elongated distal portion of the structural body. The jaw liner defines first and second inwardly-angled tissue contacting surfaces configured to oppose the ultrasonic blade in the clamping position of the jaw member. The jaw liner defines a jaw liner compliance feature disposed between the inwardly-angled tissue-contacting surfaces to facilitate outward deflection of the inwardly-angled tissue-contacting surfaces relative to one another to thereby tension tissue clamped between the jaw member and the ultrasonic blade.

In an aspect of the present disclosure, the ultrasonic blade defines a tissue-contacting surface including first and second tissue-contacting surface portions having an apex disposed therebetween. The first and second inwardly-angled tissue contacting surfaces of the jaw liner are configured to oppose the first and second tissue-contacting surface portions of the ultrasonic blade and the apex is configured to oppose the jaw liner compliance feature in the clamping position of the jaw member.

In another aspect of the present disclosure, the jaw liner compliance feature is an elongated channel extending longitudinally along the jaw liner between the first and second inwardly-angled tissue contacting surfaces thereof.

In still another aspect of the present disclosure, the elongated distal portion of the structural body defines first and second spaced-apart side rails defining an elongated opening therebetween and interconnected towards distal ends thereof via a distal cap. The jaw liner is configured for receipt within the elongated opening.

In yet another aspect of the present disclosure, the first spaced-apart rails and/or the distal cap defines a structural body compliance feature configured to facilitate outward deflection of the first and second spaced-apart side rails relative to one another, thus permitting further outward deflection of the first and second inwardly-angled tissue contacting surfaces of the jaw liner relative to one another.

In still yet another aspect of the present disclosure, each of the inwardly-angled tissue contacting surfaces of the jaw liner includes a plurality of transversely spaced-apart, longitudinally-extending grooves defined therein.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

FIG. 6 is a front, bottom, perspective view of the jaw member of the end effector assembly of the ultrasonic surgical instrument of FIG. 1;

FIG. 7 is a side, bottom, perspective view of the jaw member of the end effector assembly of the ultrasonic surgical instrument of FIG. 1;

FIG. 8 is a top, first side, perspective view of the jaw member of the end effector assembly of the ultrasonic surgical instrument of FIG. 1;

FIG. 9 is a top, second side, perspective view of the jaw member of the end effector assembly of the ultrasonic surgical instrument of FIG. 1;

FIG. 10 is a front, bottom, perspective view of another jaw member configured for use with the ultrasonic surgical instrument of FIG. 1;

FIG. 11 is a side, bottom, perspective view of the jaw member of FIG. 10; and

DETAILED DESCRIPTION

Figure 1:
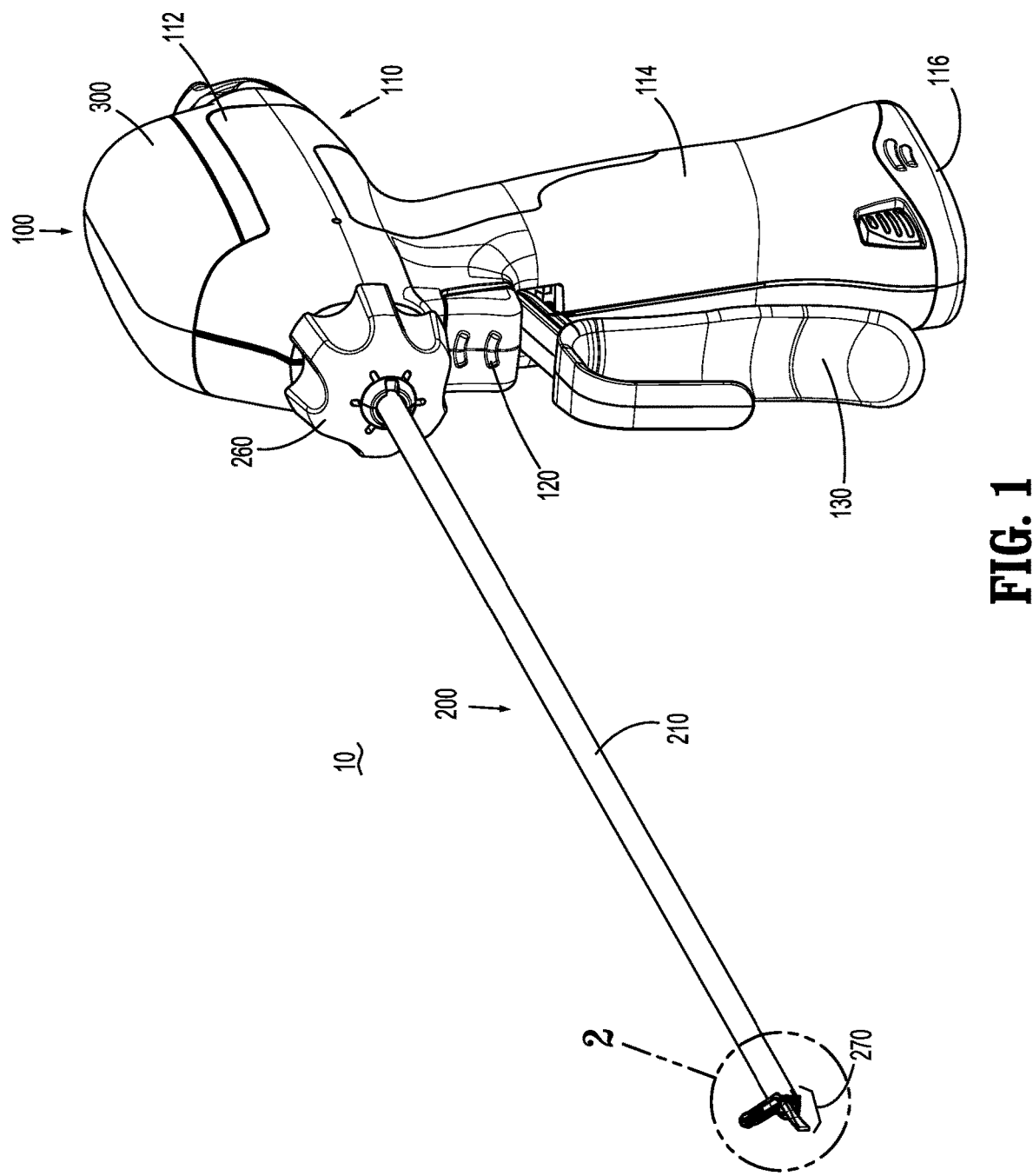
FIG. 1 is a front, perspective view of an ultrasonic surgical instrument provided in accordance with the present disclosure.

Referring generally to FIG. 1, an ultrasonic surgical instrument provided in accordance with the aspects and features of the present disclosure is shown generally identified by reference numeral 10. Although detailed with respect to ultrasonic surgical instrument 10, the aspects and features of the present disclosure are equally applicable for use with any suitable ultrasonic surgical instrument. Thus, ultrasonic surgical instrument 10 is generally described hereinbelow.

Ultrasonic surgical instrument 10 generally includes a handle assembly 100 and an elongated assembly 200 extending distally from handle assembly 100. Handle assembly 100 includes a housing 110 defining a body portion 112 configured to support an ultrasonic transducer and generator assembly ("TAG") 300, and a fixed handle portion 114 defining an internal compartment configured to receive a battery assembly (not shown). Handle assembly 100 further includes an activation button 120 operably positioned to electrically couple between TAG 300 and the battery assembly when TAG 300 is mounted on body portion 112 of housing 110 and the battery assembly is engaged within the internal compartment of fixed handle portion 114 of housing 110. A clamp trigger 130 extends from housing 110 of handle assembly 100 adjacent fixed handle portion 114 of housing 110. Clamp trigger 130 extends into body portion 112 of housing 110 and is selectively movable relative to housing 110 to actuate ultrasonic surgical instrument 10.

TAG 300 and the battery assembly, as noted above, are each removable from handle assembly 100 to facilitate disposal of handle assembly 100 after a single use or to enable sterilization of handle assembly 100 for subsequent use. TAG 300 may be configured to withstand sterilization such that TAG 300 may be sterilized for repeated use. The battery assembly, on the other hand, is configured to be aseptically transferred and retained within the internal compartment of fixed handle portion 114 of housing 110 of handle assembly 100 such that the battery assembly may be repeatedly used without requiring sterilization thereof. A locking door 116 provides selective access to the internal compartment of fixed handle portion 114 to enable the insertion and removal of the battery assembly from fixed handle portion 114 of housing 110 and retains the battery assembly within the internal compartment when disposed in the locked condition.

Activation button 120, TAG 300, and the battery assembly are electrical coupled to one another upon engagement of TAG 300 with body portion 112 of housing 110 of handle assembly 100 and engagement of the battery assembly within the internal compartment of fixed handle portion 114 of housing 110. As such, in use, when activation button 120 is activated in an appropriate manner, an underlying two-mode switch assembly (not shown) is activated to supply power from the battery assembly to TAG 300 in either a "LOW" power mode or a "HIGH" power mode, depending upon the manner of activation of activation button 120.

TAG 300 includes a generator and an ultrasonic transducer. The ultrasonic transducer converts a high voltage AC signal received from the generator into mechanical motion that is output to elongated assembly 200, as detailed below.

Figure 2:
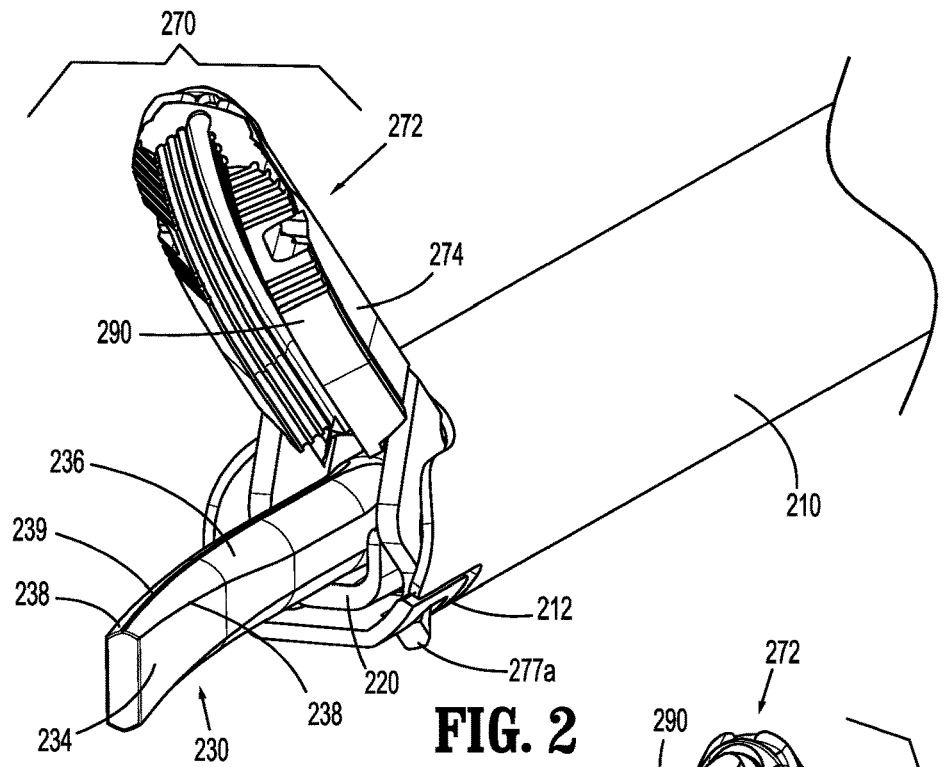
FIG. 2 is an enlarged front, perspective view of the area of detail indicated as "2" in FIG. 1 illustrating an end effector assembly of the ultrasonic surgical instrument with a jaw member of the end effector assembly disposed in an open position.
Figure 3:
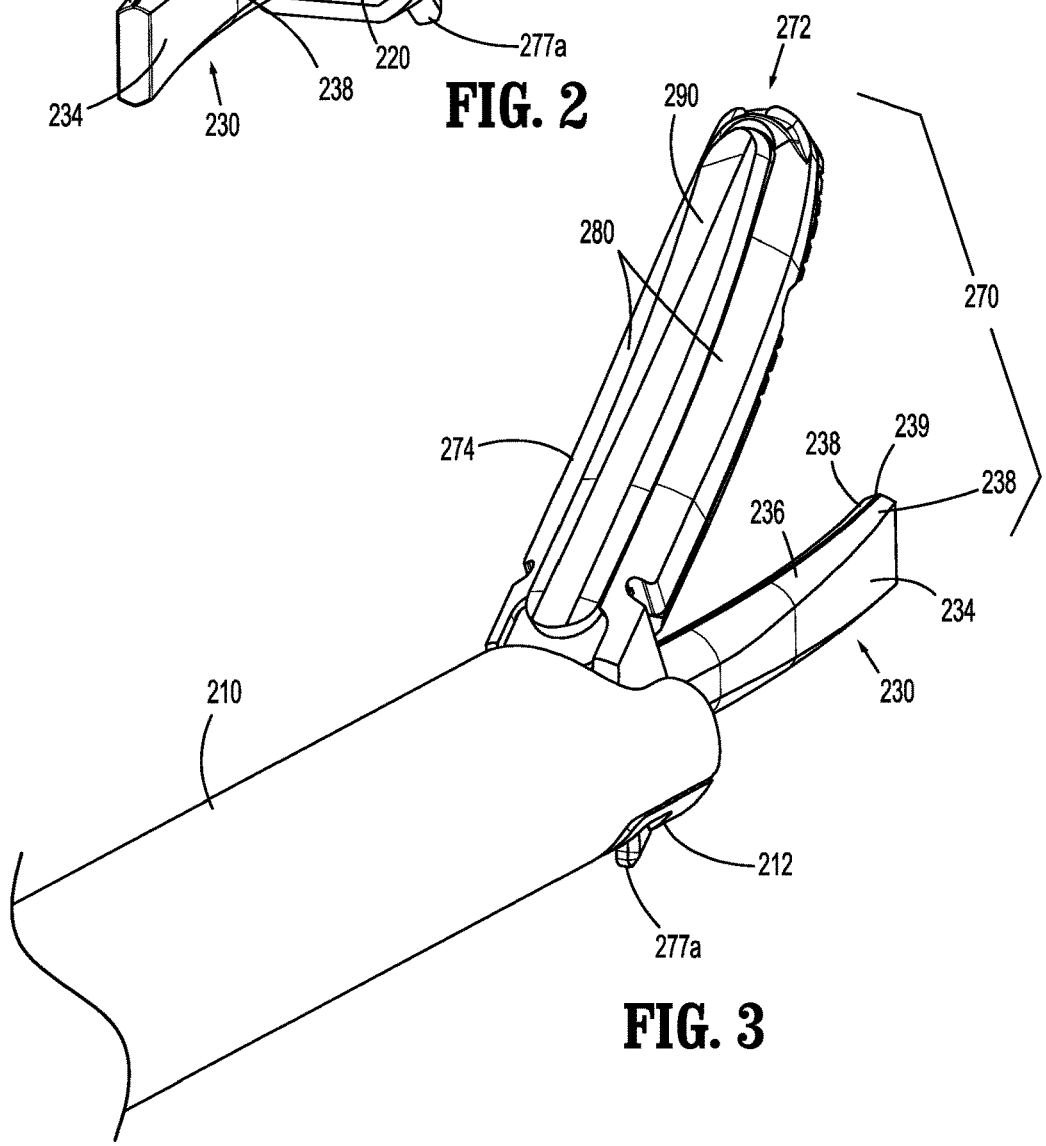
FIG. 3 is an enlarged, rear, perspective view of a distal portion of the ultrasonic surgical instrument of FIG. 1 with the jaw member disposed in the open position.
Figure 4:
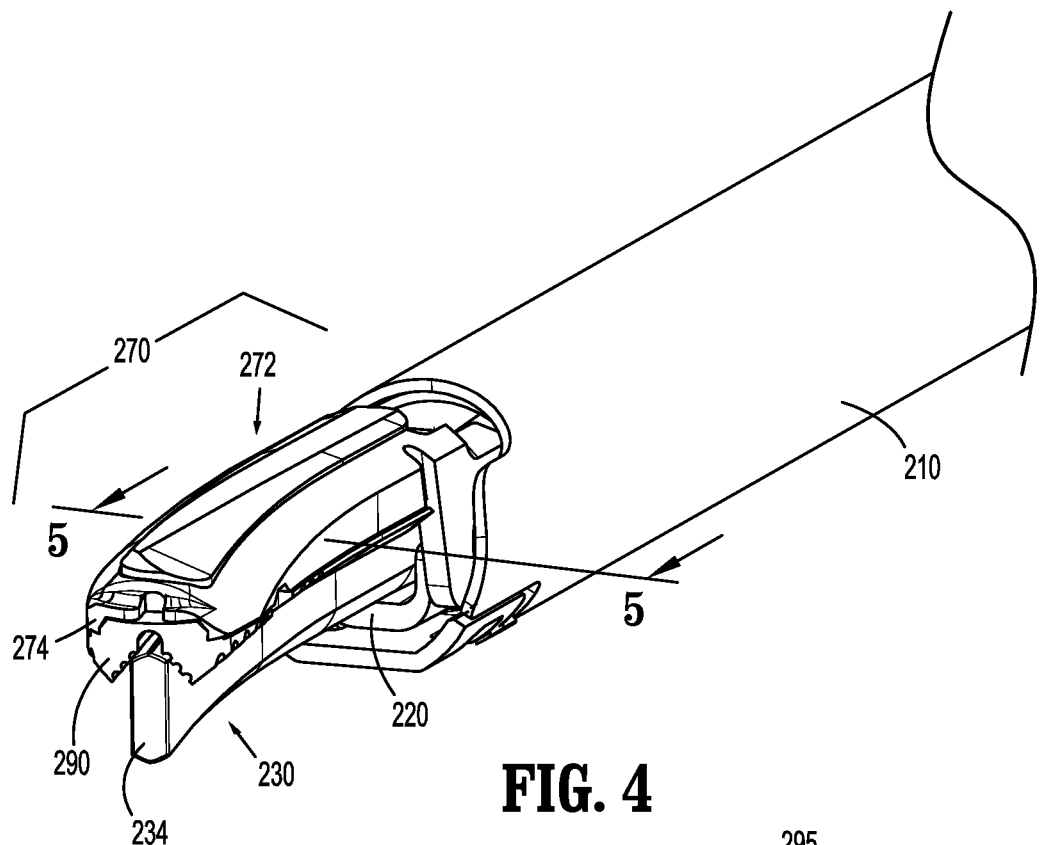
FIG. 4 is an enlarged, front, perspective view of the distal portion of the ultrasonic surgical instrument of FIG. 1 with the jaw member disposed in a clamping position.

With additional reference to FIGS. 2-4, elongated assembly 200 includes an outer drive sleeve 210, an inner support sleeve 220 disposed within outer drive sleeve 210 and about which outer drive sleeve 210 is configured to slide, a waveguide 230 extending through inner support sleeve 220, a rotation knob 260 operably coupled about proximal portions of outer and inner sleeves 210, 220, respectively, and an end effector assembly 270 disposed at the distal end of inner support sleeve 220. Elongated assembly 200 is configured such that mechanical motion output from the ultrasonic transducer of TAG 300 is transmitted along waveguide 230 to end effector assembly 270 for treating tissue therewith, such that clamp trigger 130 is selectively actuatable to manipulate end effector assembly 270, and such that rotation knob 260 is selectively rotatable to rotate elongated assembly 200 relative to handle assembly 100. Elongated assembly 200 may be configured as a disposable, single-use component or a reusable component that is sterilizable for subsequent use and may be releasably engagable with handle assembly 100 or permanently affixed thereto.

Outer drive sleeve 210 is operably coupled to clamp trigger 130 within handle assembly 100 at a proximal end portion of outer drive sleeve 210 and is operably coupled with jaw member 272 of end effector assembly 270 at a distal end portion of outer drive sleeve 210, e.g., via receipt of cam feet 277a of proximal flanges 276 of structural body 274 of jaw member 272 within apertures 212 defined within outer drive sleeve 210. Inner support sleeve 220 pivotably supports jaw member 272 at a distal end thereof, e.g., via receipt of pivot bosses 277b of proximal flanges 276 of structural body 274 of jaw member 272 within corresponding apertures (not shown) defined within inner support sleeve 220. As a result of this configuration, actuation of clamp trigger 130 translates outer drive sleeve 210 about inner support sleeve 220 and urges jaw member 272 to pivot relative to inner support sleeve 220 and blade 234 of waveguide 230 between an open position (FIG. 2) and a clamping position (FIG. 4) for clamping tissue between jaw member 272 and blade 234 of waveguide 230.

Waveguide 230 defines a body (not shown) and a blade 234 extending from the distal end of the body. The body of waveguide 230 is operably coupled to the ultrasonic transducer of TAG 300 within handle assembly 100 and extends distally from handle assembly 100 through inner support sleeve 220. Blade 234 extends from the body of waveguide 230 and distally from inner support sleeve 220 and forms part of end effector 270 in that blade 234 is positioned to oppose jaw member 272 such that pivoting of jaw member 272 from the open position (FIG. 2) to the clamping position (FIG. 4) enables clamping of tissue between jaw member 272 and blade 234. Blade 234 defines a curved configuration wherein the directions of movement of jaw member 272 between the open and clamping positions (FIGS. 2 and 4, respectively) are perpendicular to the direction of curvature of blade 234. However, it is also contemplated that blade 234 define a straight configuration or that blade 234 curve towards or away from jaw member 272, that is, where the directions of movement of jaw member 272 between the open and clamping positions (FIGS. 2 and 4, respectively) are coaxial or parallel to the direction of curvature of blade 234.

In embodiments, blade 234 defines a generally convex opposing surface 236, e.g., the surface that opposes jaw member 272. Generally convex opposing surface 236 may defined by a pair of surfaces 238 (flat or arcuate surfaces) that converge at an apex 239, or may be formed by a single arcuate surface defining an apex 239.

With reference to FIGS. 5-9, jaw member 272 includes a more-rigid structural body 274 and a more-compliant jaw liner 290. Structural body 274, as noted above, includes a pair of proximal flanges 276 each including a pivot boss 277b extending outwardly therefrom to, as noted above, enable pivotable coupling of jaw member 272 with inner support sleeve 220 (FIG. 2), and a cam foot 277a extending downwardly therefrom to, as noted above, enabling operable coupling of jaw member 272 with outer drive sleeve 210 (FIG. 2). In embodiments, a proximal bridge 277c extends between and interconnects proximal flanges 276 to provide increased structural support thereto. Structural body 274 may be formed from a relatively high-strength, more-rigid material to provide structural support such as, for example, stainless steel, or any other suitable material, and may be monolithically formed via machining, stamping, metal injection molding, or may be formed in any other suitable manner via any other suitable process.

Structural body 274 of jaw member 272 further includes an elongated distal portion 278 extending distally from the pair of proximal flanges 276. Elongated distal portion 278 defines a curved configuration similar to blade 234, e.g., wherein the directions of movement of jaw member 272 between the open and clamping positions are perpendicular to the direction of curvature of elongated distal portion 278. However, it is also contemplated that elongated distal portion 278 define a straight configuration or that elongated distal portion 278 curve towards or away from blade 234, that is, where the directions of movement of jaw member 272 between the open and clamping positions are coaxial or parallel to the direction of curvature of elongated distal portion 278.

Continuing with reference to FIGS. 5-9, elongated distal portion 278 of structural body 274, more specifically, includes a pair of spaced-apart side rails 280 each extending distally from one of the proximal flanges 276. A transverse distal cap 282 extends transversely between and interconnects the side rails 280 with one another at the distal ends thereof. As a result of the above-detailed configuration, structural body 274 defines an elongated central opening 284 extending between side rails 280 between proximal flanges 276 and transverse distal cap 282. Transverse distal cap 282 encloses the distal end of elongated central opening 284 while the proximal end of elongated central opening 284 is open as are the top and bottom of elongated central opening 284. Side rails 280 define longitudinally-extending slots 281 (FIG. 5) facing inwardly towards elongated central opening 284 along opposing sides thereof.

Referring in particular to FIG. 9, structural body 274 of jaw member 272, in embodiments, defines proximal compliance features 286 at the proximal ends of rails 280 adjacent proximal flanges 276. Proximal compliance features 286 may be formed, for example, via cut-outs formed within the proximal ends of rails 280 such that areas of reduced material thickness and structural support are formed, thus defining living hinges that allow for increased outward deflection of portions of rails 280 relative to proximal flanges 276 and one another.

Structural body 274 of jaw member 272, in embodiments, additionally or alternatively defines a distal compliance feature 288 within transverse distal cap 282, e.g., at a midpoint between rails 280. Distal compliance feature 288 may be formed, for example, via a cut-out formed within transverse distal cap 282 such that an area of reduced material thickness and structural support is formed, thus defining living a hinge that allows for increased deflection of the portions of transverse distal cap 282 disposed on either side of distal compliance feature 288 to, in turn, enable increased deflection of portions of rails 280 relative to one another and transverse distal cap 282. Other suitable features, e.g., ribs, cut-outs, etc., to facilitate compliance of structural body 274 are also contemplated.

Turning to FIGS. 5-8, jaw liner 290 may be fabricated from a compliant material such as, for example, polytetrafluoroethylene (PTFE), such that blade 234 (FIGS. 2-5) is permitted to vibrate while in contact with jaw liner 290 without damaging components of ultrasonic surgical instrument 10 (FIG. 1), e.g., structural body 274 of jaw member 272, and without compromising the hold on tissue clamped between jaw member 272 and blade 234 (FIGS. 2-5). Other suitable materials are also contemplated. Jaw liner 290 may be monolithically or otherwise formed. More specifically, jaw liner 290 may, in embodiments, be formed via injection molding in either a single-shot or multi-shot molding process. A multi-shot molding process enables different materials to be utilized, e.g., a first material used to form base 291 and a second material used to form arms 292. Different materials for jaw liner 290 may be used, for example, to facilitate tissue tensioning, as detailed below.

Jaw liner 290 defines a generally Y-shaped configuration including a base 291 and first and second arms 292 extending from base 291 and apart from one another at an angle relative to base 291. As such, arms 292 define inner, inwardly-angled surfaces 293, which may be arcuate or flat. In embodiments, arms 292 are configured such that inner, inwardly-angled surfaces 293 are complementary with respective opposing surfaces 238 of blade 234 (see FIG. 5).

Figure 5:
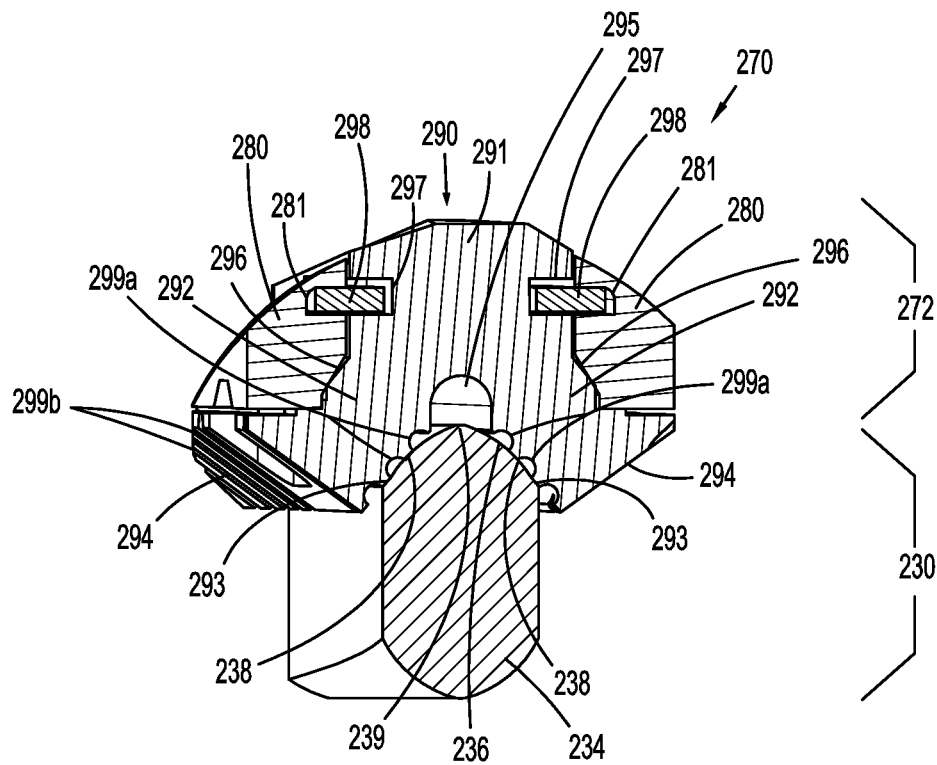
FIG. 5 is a transverse, cross-sectional view taken along section line "5-5" of FIG. 4.

Arms 292 further define bottom, outwardly-angled surfaces 294 (which may be concave or flat) extending outwardly from inner, inwardly-angled surfaces 293 such that inner and bottom surfaces 293, 294 cooperate to define a W-shaped transverse, cross-sectional exposed surface outline of jaw liner 290 (see FIG. 5). A compliance feature 295 in the form of a longitudinally-extending channel is defined within jaw liner 290 between the inner, inwardly-angled surfaces 293. More specifically, rather than the inner, inwardly-angled surfaces 293 extending to meet one another, compliance feature 295 is defined therebetween to allow for increased deflection of first and second arms 292 of jaw liner 290 relative to one another, thereby increasing tension on tissue clamped between blade 234 and jaw member 272 (see FIG. 5), as detailed below. In embodiments, compliance features 295 is generally aligned with apex 239 of blade 234 in the clamping position of jaw member 272 (see FIG. 5).

Referring to FIG. 5, jaw liner 290 further includes outer, back surfaces 296 defining the outer sides of base 291 and arms 292. Outer, back surfaces 296 are configured to mate with the inner and bottom surfaces of side rails 280 of elongated distal portion 278 of structural body 274 of jaw member 272 upon insertion of jaw liner 290 into elongated central opening 284 of elongated distal portion 278 of structural body 274. Base 291 of jaw liner 290 further includes longitudinally-extending slots 297 defined within the outer, back surfaces 296 thereof that are configured to align with slots 281 of side rails 280 upon insertion of jaw liner 290 into elongated central opening 284. With slots 281, 297 aligned with one another, a retention clip 298 is engaged within slots 281, 297, e.g., via sliding of retention clip 298 into slots 281, 297 in a proximal-to-distal direction, thereby retaining jaw liner 290 in engagement with structural body 274. Other configurations for retaining jaw liner 290 in engagement with structural body 274 are also contemplated such as, for example, a snap-fit engagement, overmolding jaw liner 290 onto structural body 274, pad printing jaw liner 290 onto structural body 274, etc.

With reference to FIGS. 6 and 7, in embodiments, inner, inwardly-angled surfaces 293 each define a plurality of transversely-spaced, longitudinally-extending grooves 299a. Grooves 299a, as detailed below, facilitate tensioning of tissue clamped between jaw member 272 and blade 234 (see FIG. 5). Additionally or alternatively, bottom, outwardly-angled surfaces 294 define longitudinally-spaced, transversely-extending grooves 299b configured to facilitate grasping of tissue and inhibiting slippage of tissue clamped between jaw member 272 and blade 234 (see FIG. 5).

Referring generally to FIGS. 1-9, in use, ultrasonic instrument 10 is advanced into a surgical site and manipulated such that end effector 270 is positioned with tissue to be treated disposed between jaw member 272 and blade 234 with jaw member 272 disposed in the open position (FIGS. 1-3). Thereafter, clamp trigger 130 is squeezed towards fixed handle portion 114 of housing 110 from an un-actuated position to an actuated position to translate outer drive sleeve 210 about inner support sleeve 220 and relative to end effector assembly 270, thereby pivoting jaw member 272 relative to blade 234 from the open position towards the clamped position (FIGS. 4 and 5) to clamp tissue between jaw member 272 and blade 234 and, more specifically, between inner, inwardly-facing surfaces 293 of jaw liner 290 of jaw member 272 and opposing surface 236 of blade 234. Bottom, outwardly-facing surfaces 294 (and, more specifically, grooves 299b thereof) of jaw liner 290 facilitate grasping of tissue and inhibiting slippage of tissue on either side of blade 234.

Referring to FIG. 5, as jaw member 272 is urged towards the clamped position to apply a clamping force to tissue, blade 234 and tissue provide an opposing force resisting clamping of jaw member 272. As a result of this opposing force, jaw liner 290 is compressed due to the compliant nature thereof and first and second arms 292 of jaw liner 290 are deflected outwardly apart from one another at compliance feature 295 and, in embodiments where provided, facilitated via the outward deflection of side rails 280 of elongated distal portion 278 of structural body 274 (enabled via the living hinges formed at compliance features 286, 288), such that tissue is tensioned across apex 239 of blade 234. Grooves 299a, as noted above, facilitate tensioning of tissue across apex 239 of blade 234 by holding tissue in position relative to arms 292 such that tissue is pulled and tensioned upon the outward deflection of arms 292.

With tissue clamped in the manner detailed above, a first portion of tissue is grasped between the inwardly-facing surface 293 of the first arm 292 of jaw liner 290 and the opposing surface 238 of blade 234, a second portion of tissue is grasped between the inwardly-facing surface 293 of the second arm 292 of jaw liner 290 and the opposing surface 238 of blade 234, and the interconnecting portion of tissue extending between the first and second portions extends across apex 239 of blade and compliance features 295 of jaw liner 290 under increased tension.

Referring also to FIG. 1, with tissue clamped as detailed above, blade 234 may be activated, e.g., via depression of activation button 120, to supply ultrasonic energy from TAG 300, along the waveguide, to blade 234. The ultrasonic energy provided at blade 234 is used to heat and, ultimately, seal the first and second portions of tissue. Further, facilitated by the increased tension of the interconnecting portion of tissue, the ultrasonic energy applied to the interconnecting portion of tissue cuts the interconnecting potion of tissue, thereby separating the sealed first and second portions of tissue from one another.

Figure 12:
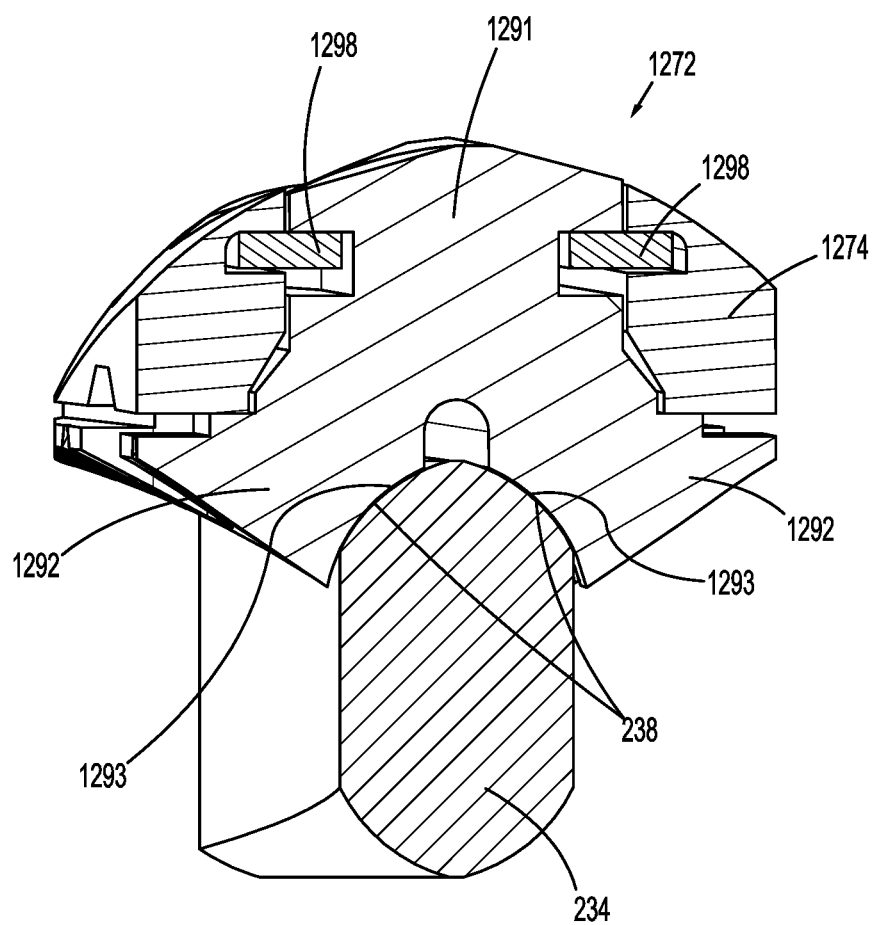
FIG. 12 is a transverse, cross-sectional view of the jaw member of FIG. 10.

Turning to FIGS. 10-12, another embodiment of a jaw member 1272 is shown configured for use with ultrasonic instrument 10 (FIG. 1) or any other suitable ultrasonic instrument. Jaw member 1272 is similar to jaw member 272 (FIGS. 5-9), except with respect to the configuration of jaw liner 1290 thereof. Thus, only differences between jaw liner 1290 and jaw liner 290 (FIGS. 5-9) are described in detail hereinbelow while similarities are omitted or summarily described.

Jaw member 1272 includes a more-rigid structural body 1274, a more-compliant jaw liner 1290, and a retention clip 1298 (FIG. 12) configured to retain jaw liner 1290 in engagement with structural body 1274. Jaw liner 1290 defines a generally Y-shaped configuration including a base 1291 and first and second arms 1292 extending from base 1291 and apart from one another. Arms 1292 define inner, inwardly-angled surfaces 1293 that are concave and generally smooth. That is, inner, inwardly-angled surfaces 1293 are smooth as compared to inner, inwardly-angled surfaces 293 which include grooves 299a (see FIG. 5). Concave surfaces 1293 are complementary to the convex opposing surface 238 of blade 234. Jaw liner 1290 is otherwise similar and may include any of the features of jaw liner 290 (FIGS. 5-9) detailed above.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly of an ultrasonic surgical instrument, the end effector assembly comprising:
   an ultrasonic blade defining a tissue-contacting surface; and
   a jaw member pivotable relative to the ultrasonic blade between an open position and a clamping position, the jaw member including:
      a structural body including a pair of proximal flanges and an elongated distal portion extending distally from the pair of proximal flanges, the elongated distal portion including first and second spaced-apart side rails defining an elongated opening therebetween and interconnected at distal ends thereof via a distal cap; and
      a jaw liner engaged within the elongated opening, the jaw liner defining first and second inwardly-angled tissue contacting surfaces and a jaw liner compliance feature, the first and second inwardly-angled tissue contacting surfaces defining a volume therebetween and configured to oppose the tissue-contacting surface of the ultrasonic blade in the clamping position of the jaw member, wherein the jaw liner compliance feature includes an elongated channel defined within the jaw liner in at least an outwardly-flexed condition of the jaw liner, the elongated channel extending longitudinally along the jaw liner and recessed relative to an entirety of the volume defined between the first and second inwardly-angled tissue contacting surfaces with the first and second inwardly-angled tissue contacting surfaces disposed on opposing sides of the elongated channel, the jaw liner compliance feature configured to facilitate outward deflection of the inwardly-angled tissue-contacting surfaces relative to one another from an at-rest condition of the jaw liner to the outwardly-flexed condition of the jaw liner to thereby tension tissue clamped between the jaw member and the ultrasonic blade.

2. The end effector assembly according to claim 1, wherein the tissue-contacting surface of the ultrasonic blade includes first and second tissue-contacting surface portions having an apex disposed therebetween, the first and second inwardly-angled tissue contacting surfaces of the jaw liner configured to oppose the first and second tissue-contacting surface portions of the ultrasonic blade and the apex configured to oppose the jaw liner compliance feature in the clamping position of the jaw member.

3. The end effector assembly according to claim 1, wherein the first and second spaced-apart side rails define first and second structural body compliance features configured to facilitate outward deflection of the first and second spaced-apart side rails relative to one another, thus permitting further outward deflection of the first and second inwardly-angled tissue contacting surfaces of the jaw liner relative to one another.

4. The end effector assembly according to claim 3, wherein the first and second structural body compliance features are cut-outs defined within the first and second spaced-apart side rails towards proximal ends thereof.

5. The end effector assembly according to claim 1, wherein the distal cap of the structural body defines a third structural body compliance feature configured to facilitate outward deflection of the first and second spaced-apart side rails relative to one another, thus permitting further outward deflection of the first and second inwardly-angled tissue contacting surfaces of the jaw liner relative to one another.

6. The end effector assembly according to claim 1, wherein each of the inwardly-angled tissue contacting surfaces of the jaw liner includes a plurality of transversely spaced-apart, longitudinally-extending grooves defined therein.

7. The end effector assembly according to claim 1, wherein the jaw liner is formed from a compliant material.

8. The end effector assembly according to claim 7, wherein the compliant material is PTFE.

9. The end effector assembly according to claim 1, wherein the elongated channel is defined within the jaw liner in each of the at-rest condition and the outwardly-flexed condition of the jaw liner.

10. An ultrasonic surgical instrument, comprising:
the end effector assembly according to claim 1;
an ultrasonic transducer; and
an ultrasonic waveguide operably coupling the ultrasonic transducer with the ultrasonic blade of the end effector assembly.

11. The ultrasonic surgical instrument according to claim 10, further comprising an ultrasonic generator configured to drive the ultrasonic transducer.

12. An end effector assembly of an ultrasonic surgical instrument, the end effector assembly comprising:
an ultrasonic blade including a tissue-contacting surface defined by a pair of surfaces that converge at an apex; and
a jaw member pivotable relative to the ultrasonic blade between an open position and a clamping position, the jaw member including:
a structural body defining an elongated opening and including at least one living hinge defined in the structural body; and
a jaw liner engaged within the elongated opening, the jaw liner defining a jaw liner compliance feature including a longitudinally-extending channel in at least an outwardly-flexed condition of the jaw liner, the jaw liner compliance feature recessed into the jaw liner and configured for positioning in substantial alignment with the apex in the clamping position of the jaw member, the jaw liner compliance feature and the at least one living hinge configured to facilitate outward deflection of opposing portions of the jaw liner on either side of the longitudinally-extending channel to transition the jaw liner from an at-rest condition to the outwardly-flexed condition to tension tissue clamped between the jaw member and the ultrasonic blade.

13. The end effector assembly according to claim 12, wherein the structural body includes a pair of proximal flanges configured to facilitate pivoting of the jaw member relative to the ultrasonic blade.

14. The end effector assembly according to claim 12, wherein the structural body includes an elongated distal portion including first and second spaced-apart side rails defining the elongated opening therebetween.

15. The end effector assembly according to claim 12, wherein the structural body is formed from a material that is more-rigid and wherein the jaw liner is formed from a material that is more-compliant.

16. The end effector assembly according to claim 15, wherein the structural body is formed from stainless steel and the jaw liner is formed from PTFE.

17. The end effector assembly according to claim 12, wherein the opposing portions of the jaw liner on either side of the longitudinally-extending channel include first and second inwardly-angled tissue contacting surfaces configured to oppose the pair of surfaces of the tissue-contacting surface of the ultrasonic blade in the clamping position of the jaw member.

18. The end effector assembly according to claim 12, wherein the at least one living hinge includes first and second living hinges on opposing sides of the structural body.

19. The end effector assembly according to claim 12, wherein the at least one living hinge includes a living hinge at a distal end portion of the structural body.

20. The end effector assembly according to claim 12, wherein a tissue-contacting surface of the jaw liner defines a plurality of transversely spaced-apart, longitudinally-extending grooves defined therein.

21. The end effector assembly according to claim 12, wherein the elongated channel is defined within the jaw liner in each of the at-rest condition and the outwardly-flexed condition of the jaw liner.

22. An ultrasonic surgical instrument, comprising:
the end effector assembly according to claim 12;
an ultrasonic transducer; and
an ultrasonic waveguide operably coupling the ultrasonic transducer with the ultrasonic blade of the end effector assembly.

23. The ultrasonic surgical instrument according to claim 22, further comprising an ultrasonic generator configured to drive the ultrasonic transducer.

* * * * *